United States Patent
Yoshida

(10) Patent No.: US 11,457,885 B2
(45) Date of Patent: Oct. 4, 2022

(54) IMAGE PROCESSING APPARATUS

(71) Applicant: Shimadzu Corporation, Kyoto (JP)

(72) Inventor: Takanori Yoshida, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 240 days.

(21) Appl. No.: 16/915,406

(22) Filed: Jun. 29, 2020

(65) Prior Publication Data

US 2021/0085270 A1 Mar. 25, 2021

(30) Foreign Application Priority Data

Sep. 19, 2019 (JP) .............................. JP2019-170164

(51) Int. Cl.
*A61B 6/00* (2006.01)
*G06T 11/60* (2006.01)
*G06T 7/00* (2017.01)
*G06V 10/25* (2022.01)

(52) U.S. Cl.
CPC ............. *A61B 6/463* (2013.01); *A61B 6/504* (2013.01); *A61B 6/507* (2013.01); *G06T 7/0012* (2013.01); *G06T 11/60* (2013.01); *G06V 10/25* (2022.01); *G06T 2207/10116* (2013.01); *G06T 2207/30104* (2013.01)

(58) Field of Classification Search
None
See application file for complete search history.

(56) References Cited

U.S. PATENT DOCUMENTS

2010/0259550 A1* 10/2010 Baumgart ............. A61B 6/463
345/157
2015/0150526 A1 6/2015 Ohishi
2019/0103184 A1* 4/2019 Kajiki ................... G16H 15/00

FOREIGN PATENT DOCUMENTS

JP 2015-126868 A 7/2015

* cited by examiner

*Primary Examiner* — Hoon K Song
(74) *Attorney, Agent, or Firm* — Muir Patent Law, PLLC

(57) ABSTRACT

This image processing apparatus is provided with an image acquisition unit for generating a concentration change image and a control unit for performing control for displaying a blood vessel image and a concentration change image, and the control unit is configured to perform control for accepting a selection of a target region on the blood vessel image displayed on the display unit and for displaying the concentration change image corresponding to the selected target region.

13 Claims, 10 Drawing Sheets

IMAGE PROCESSING APPARATUS

CROSS-REFERENCE TO RELATED APPLICATIONS

The related application number JP2019-170164, entitled "Image Processing Apparatus" filed on Sep. 19, 2019, and invented by Takanori Yoshida, upon which this patent application is based, is hereby incorporated by reference.

BACKGROUND OF THE INVENTION

Field of the Invention

The present invention relates to an image processing apparatus.

Conventionally, a medical image processing apparatus for generating blood vessel image data having a pixel value corresponding to a concentration of a contrast agent is known. Such a device is disclosed in, for example, Japanese Unexamined Patent Application No. 2015-126868.

The medical image processing apparatus disclosed in the above-described Japanese Unexamined Patent Application No. 2015-126868 is provided with a blood vessel image data generation unit and a display unit. The blood vessel image data generation unit generates a concentration change profile representing the relationship between the concentration of the contrast agent and the time when the contrast agent flowed in and out, and generates a blood vessel image data displayed in color according to a particular phase, such as the arrival phase of the contrast agent from the concentration change profile, while the display unit displays the generated blood vessel image data.

Note that in some cases, for the purpose of grasping the degree of restoration of the blood flow before and after a blood vessel intervention treatment, it is desired to grasp the blood flow velocity in the target region of the blood vessel. However, in the above-described medical image processing apparatus described in Japanese Unexamined Patent Application No. 2015-126868, the user can merely obtain the information about the particular time phase, such as the arrival time phase of the contrast agent, from the displayed blood vessel image data, and cannot intuitively grasp the blood flow velocity in the target region of the blood vessel.

SUMMARY OF THE INVENTION

The present invention has been made to solve the above-mentioned problems, and an object of the present invention is to provide an image processing apparatus capable of intuitively grasping a blood flow velocity in a target region of a blood vessel by a user.

In order to achieve the above-described objects, the image processing apparatus according to one aspect of the present invention is provided with an imaging unit including an X-ray irradiation unit configured to emit X-rays to a subject and a detection unit configured to detect the X-rays transmitted through the subject to acquire a detection signal; an image acquisition unit configured to acquire a blood vessel image of the subject based on the detection signal and generate a concentration change image including a graph image indicating a temporal change of a value related to a concentration of a contrast agent administered to a blood vessel of the subject; and a control unit configured to perform control for displaying the blood vessel image and the concentration change image on a display unit. The control unit is configured to perform control for accepting a selection of a target region on the blood vessel image displayed on the display unit and perform control for displaying the concentration change image corresponding to the selected target region.

According to one aspect of the present invention, as described above, the control unit is configured to perform control for accepting a selection of a target region on a blood vessel image displayed on a display unit and control for displaying a concentration change image corresponding to the selected target region. With this configuration, the concentration change image corresponding to the target region selected on the blood vessel image is displayed, so that the user can intuitively grasp the blood flow velocity in the target region of the blood vessel from the concentration change image.

DESCRIPTION OF THE PREFERRED EMBODIMENT

Hereinafter, an embodiment in which the present invention is embodied will be described with reference to the attached drawings.

(Configuration of Image Processing Apparatus)

Figure 1:
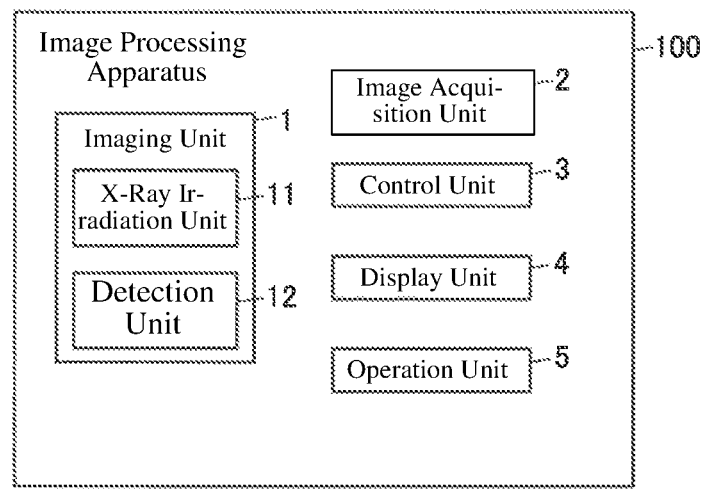
FIG. 1 is a block diagram showing an image processing apparatus.

As shown in FIG. 1, the image processing apparatus 100 in this embodiment is provided with an imaging unit 1, an image acquisition unit 2, a control unit 3, a display unit 4, and an operation unit 5. In this embodiment, the image processing apparatus 100 is used for a diagnosis or a treatment of a patient who is a subject 50 (see FIG. 2).

Figure 2:
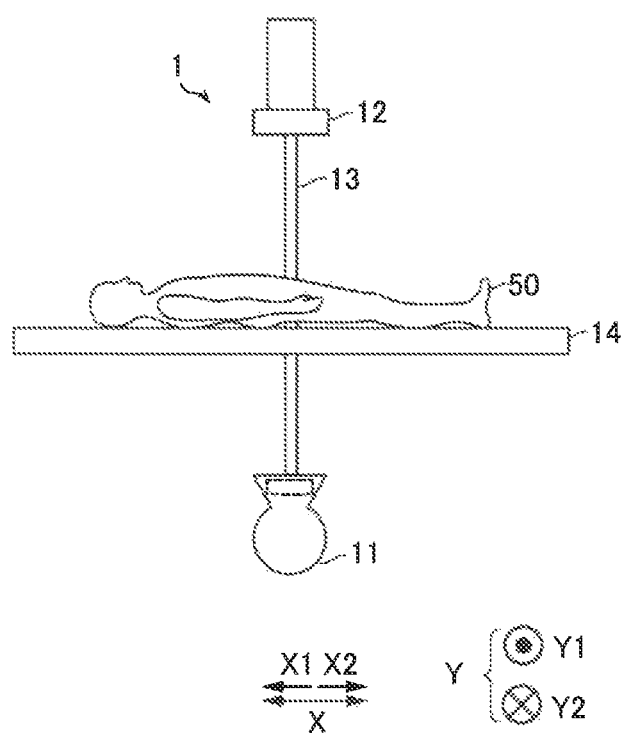
FIG. 2 is a diagram for explaining an imaging unit.

As shown in FIG. 2, the imaging unit 1 is provided with an X-ray irradiation unit 11 for irradiating the subject 50 with X-rays and a detection unit 12 for detecting the X-rays transmitted through the subject 50.

The X-ray irradiation unit 11 is attached to one tip of an arm 13. The X-ray irradiation unit 11 is configured to emit X-rays when a voltage is applied by a drive unit (not shown). The X-ray irradiation unit 11 has a collimator (not shown) which is capable of adjusting the irradiation field which is the irradiation range of the X-rays.

The detection unit 12 is arranged at the tip of the arm 13 opposite to the X-ray irradiation unit 11 with a top board 14 on which the subject 50 is placed interposed therebetween. The detection unit 12 is composed of, for example, an FPD (flat panel detector). The detection unit 12 outputs a detection signal based on the detected X-rays.

The image processing apparatus 100 is configured such that the relative position between the imaging unit 1 and the top board 14 can be changed by moving the imaging unit 1 by a moving device (not shown).

As shown in FIG. 1, the image acquisition unit 2 is a GPU (Graphics Processing Unit) or an FPGA (Field-Programmable Gate Array) configured for imaging. The image acquisition unit 2 generates an X-ray image based on a detection signal output from a detection unit 12 by executing an image processing program. In this embodiment, the X-ray image is a blood vessel image 23 of the blood vessel 51 of the lower limb of the subject 50.

Figure 3:
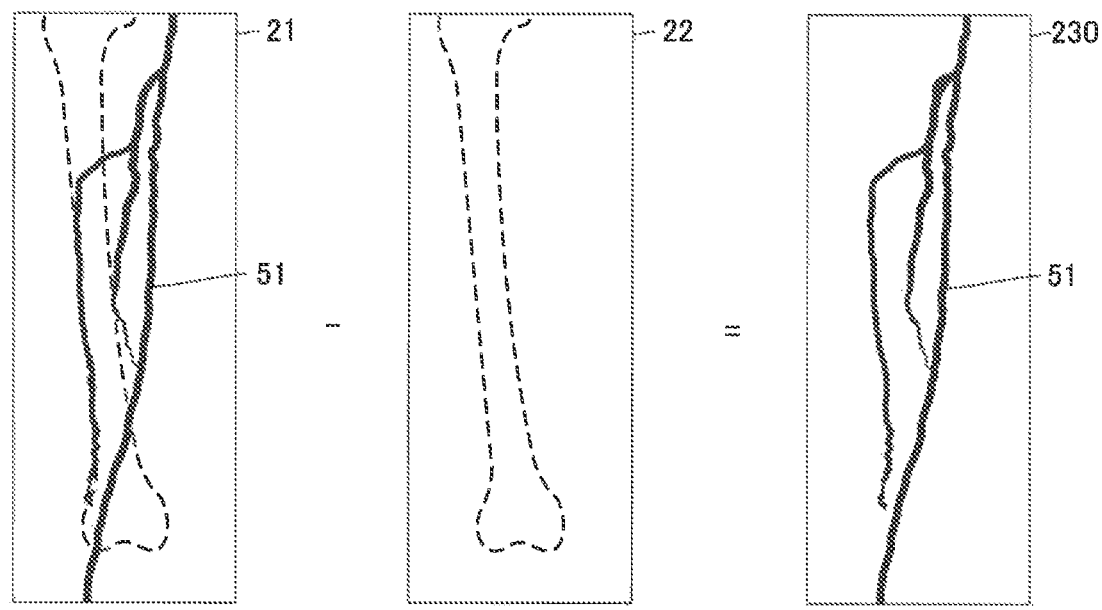
FIG. 3 is a diagram for explaining a subtraction image.

As shown in FIG. 3, in this embodiment, a subtraction image 230 obtained by subtracting the non-contrast agent image 22 which is an X-ray image captured without administering a contrast agent to the subject 50 from the contrast agent image 21 which is an X-ray image captured by administering a contrast agent to the subject 50 is used as a blood vessel image 23. The contrast agent is used to increase the X-ray absorption rate of the blood vessel 51. The non-contrast agent image 22 is a bone image in which the blood vessel 51 is not reflected (is not clearly reflected). The contrast agent image 21 is an image in which the blood vessel 51 is imaged. By subtracting the non-contrast agent image 22 from the contrast agent image 21, the portion having the same pixel value in the contrast agent image 21 and the non-contrast agent image 22 is removed, so that the blood vessel image 23 which is a clear image of the blood vessel 51 can be acquired.

The image acquisition unit 2 generates the blood vessel image 23 in which the velocity is displayed in a visually recognizable manner in response to the velocity of the contrast agent flowing in the target region 24 (see FIG. 5) from the captured blood vessel image 23. The image acquisition unit 2 processes the blood vessel image 23 so as to display a point at which the flowing velocity of the contrast agent is fast in red and a point at which the flowing velocity is slow in blue. Note that the target region 24 denotes a region of a part of the blood vessel 51 included in the blood vessel image 23, and is a target region of a treatment or a diagnosis.

Figure 4:
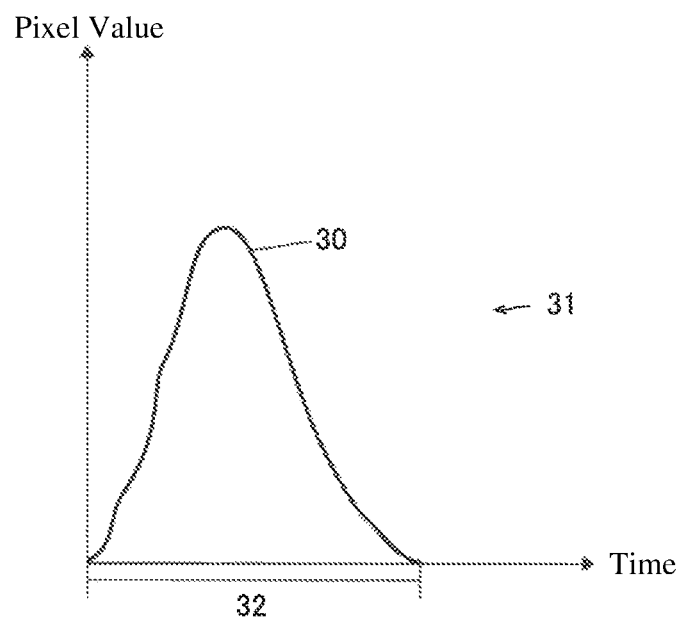
FIG. 4 is a diagram showing an example of a concentration change image.

As shown in FIG. 4, the image acquisition unit 2 generates a concentration change image 31 including the graph image 30 indicating the temporal change of the numerical value regarding the concentration of the contrast agent administered to the blood vessel 51 of the subject 50 in the target region 24 of the blood vessel image 23. In this embodiment, the numerical value regarding the concentration of the contrast agent is a pixel value of the target region 24. The graph image 30 is an image of a waveform representing the concentration change of the contrast agent.

As shown in FIG. 4, the horizontal axis of the graph image 30 represents the time after the administration of the contrast agent. The vertical axis represents the magnitude of the pixel value in the target region 24. Since the blood vessel 51 in the target region 24 effectively absorbs the X-rays irradiated from the X-ray irradiation unit 11 as the concentration of the contrast agent increases, the detection unit 12 does not detect the X-rays and therefore the pixel value decreases (it becomes dark). Therefore, the graph image 30 sets the origin of the vertical axis to the maximum value of the pixel value.

When the flowing velocity of the contrast agent is high, the width 32 of the time in the graph image 30 becomes small. The width 32 of the time is defined from the rising position at which the numerical value regarding the concentration of the contrast agent starts to rise until the numerical value regarding the contrast agent decreases through the maximum peak position and becomes approximately in parallel to the horizontal axis or crosses the horizontal axis due to completion of the flow of the contrast agent.

The control unit 3 is composed of a CPU (Central Processing Unit). The control unit 3 performs control regarding the operation of the image processing apparatus 100.

Figure 6:
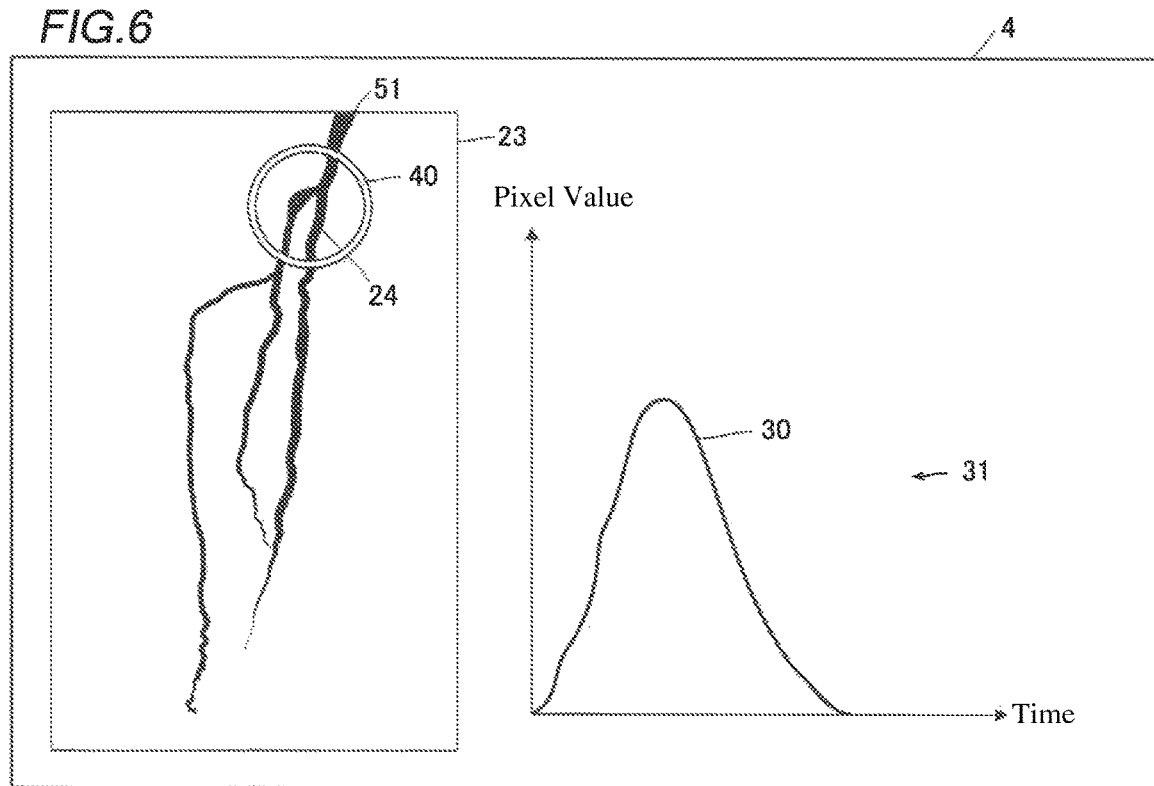
FIG. 6 is a diagram showing an example of an image displayed on a display unit.

As shown in FIG. 1 and FIG. 6, the display unit 4 is, for example, a monitor, such as a liquid crystal display. The display unit 4 shows a blood vessel image 23 and a concentration change image 31. The blood vessel image 23 and the concentration change image 31 may be displayed simultaneously or separately. Note that one display unit 4 may be provided or a plurality of display units 4 may be provided.

As shown in FIG. 1, the operation unit 5 is a touch panel provided on the image processing apparatus 100. By manipulating the operation unit 5, a user performs a selection of the blood vessel image 23 and a selection of the target region 24.

As shown in FIG. 1 and FIG. 2, when imaging the blood vessel 51 of the lower limb, a contrast agent is administered to the subject 50. The control unit 3 controls the imaging unit 1 so as to capture the contrast agent image 21 while moving the imaging unit 1 in the X-direction and Y-direction in accordance with the flow of the contrast agent flowing through the blood vessel 51. Further, the control unit 3 performs control for making the image processing apparatus 100 store the imaging conditions, such as, e.g., the intensity of X-rays, the irradiation angle of X-rays, and the imaging rate.

Figure 5:
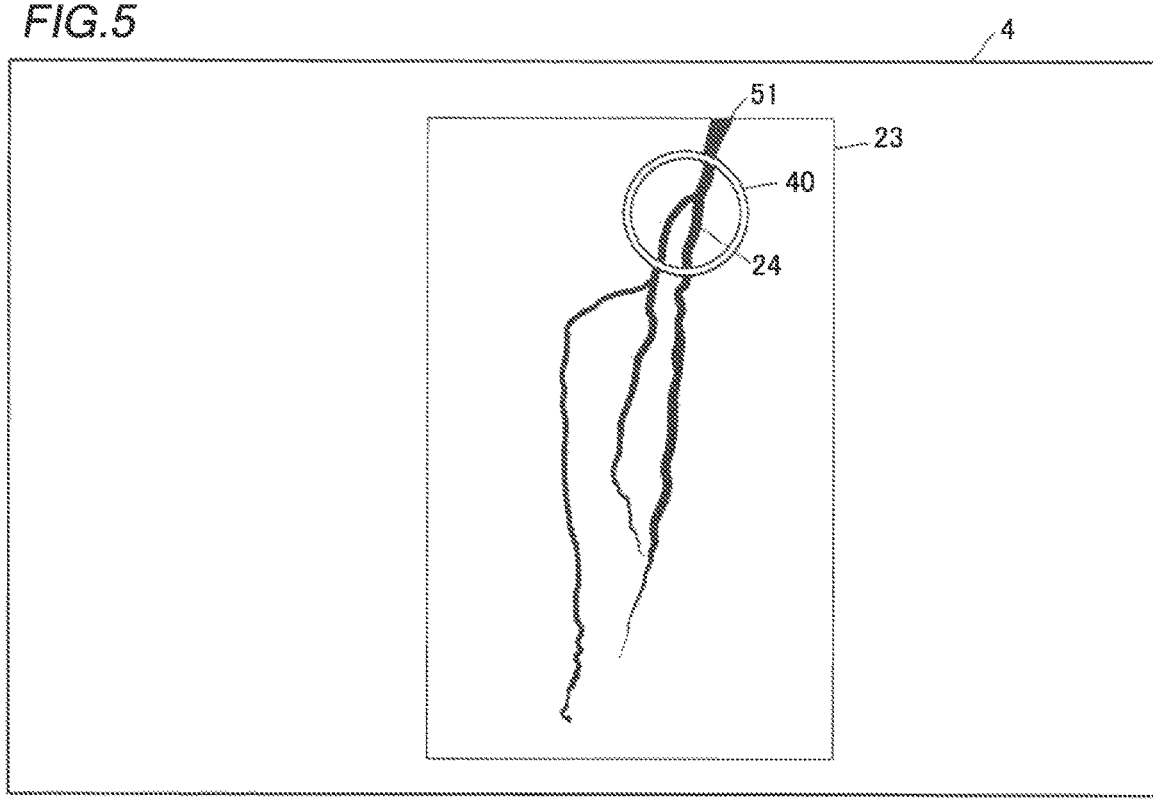
FIG. 5 is a diagram showing an example of a region specification image.

As shown in FIG. 5, the control unit 3 performs control for displaying the blood vessel image 23 generated by the image acquisition unit 2 on the display unit 4. The control unit 3 performs control for displaying the concentration change image 31 corresponding to the selected target region 24 when the operation input for selecting the target region 24 by the operation unit 5 by the user is accepted or when the target region 24 is selected on the blood vessel image 23 displayed on the display unit 4 based on the default set in the image processing apparatus 100 in advance.

As shown in FIG. 5, the control unit 3 performs control for displaying on the display unit 4 an image in which the blood vessel image 23 and the selected region specification image 40 are superimposed.

As shown in FIG. 6, when the target region 24 of the blood vessel image 23 is selected, the control unit 3 performs control for displaying on the display unit 4 the concentration change image 31 including the graph image 30 corresponding to the determined target region 24. In the display unit 4, the blood vessel image 23 and the concentration change image 31 are displayed side by side. At this time, the image acquisition unit 2 averages the pixel values included within the region specification image 40 and generates the concentration change image 31 based on the average value. Note that the average value is an example of "representative value" recited in claims.

(Generation of Concentration Change Image)

Figure 7:
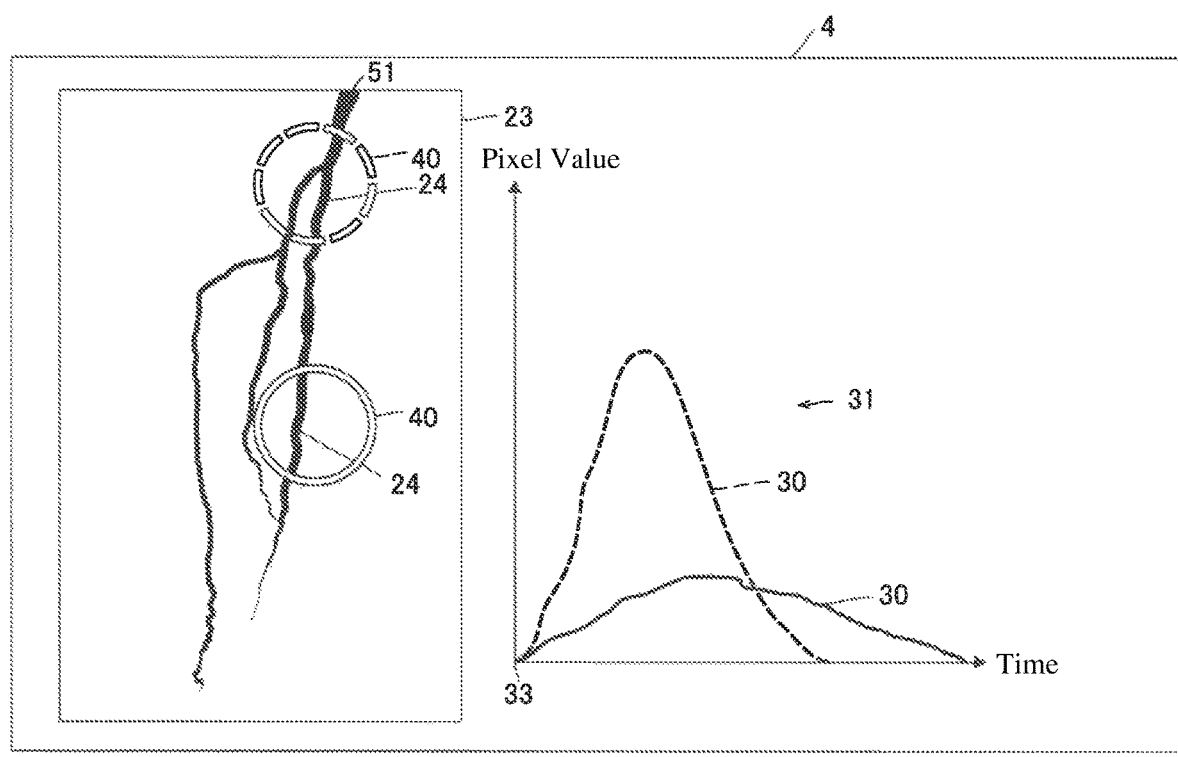
FIG. 7 is a diagram showing an example of a blood vessel image in which a plurality of target regions is selected.

Referring to FIG. 7, the generation of a concentration change image 31 when a plurality of target regions 24 is selected on the blood vessel image 23 will be described. When a plurality of target regions 24 of the blood vessel image 23 is selected, the image acquisition unit 2 generates a concentration change image 31 in which graph images 30 are superimposed with their reference points 33 aligned. Note that the reference point 33 is a rising position of the graph image 30 at which the pixel value starts to increase. In FIG. 7, the graph image 30 corresponding to the target region 24 in which the region specification image 40 is represented by a dashed line is represented by a dashed line, and the graph image 30 corresponding to the target region 24 in which the region specification image 40 is represented by a solid line is represented by a solid line.

The control unit 3 performs control for displaying on the display unit 4 the concentration change image 31 in which the graph images 30 corresponding to the respective selected target regions 24 are superimposed.

Figure 8:
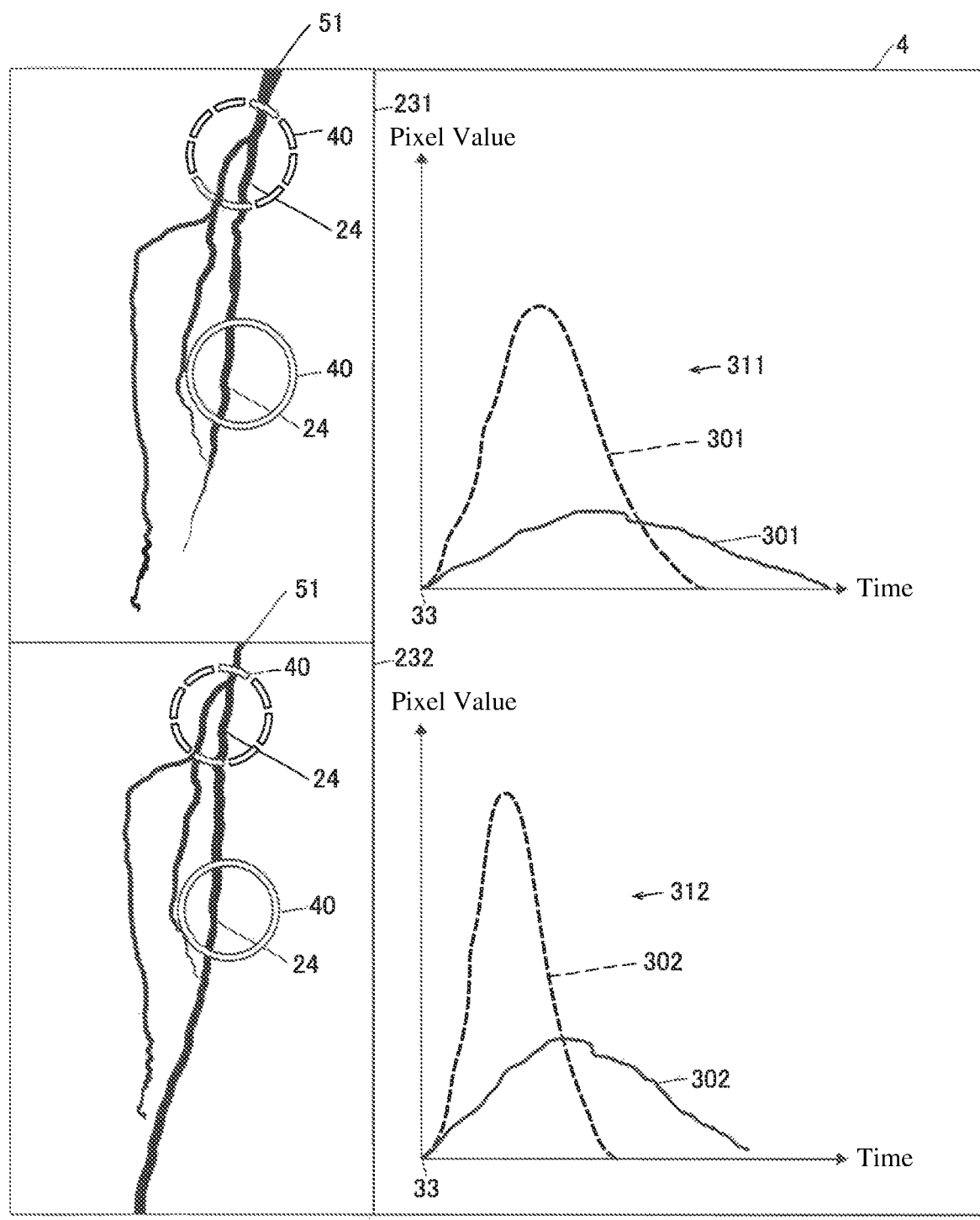
FIG. 8 is a diagram showing an example of a first blood vessel image and a second blood vessel image.
Figure 9:
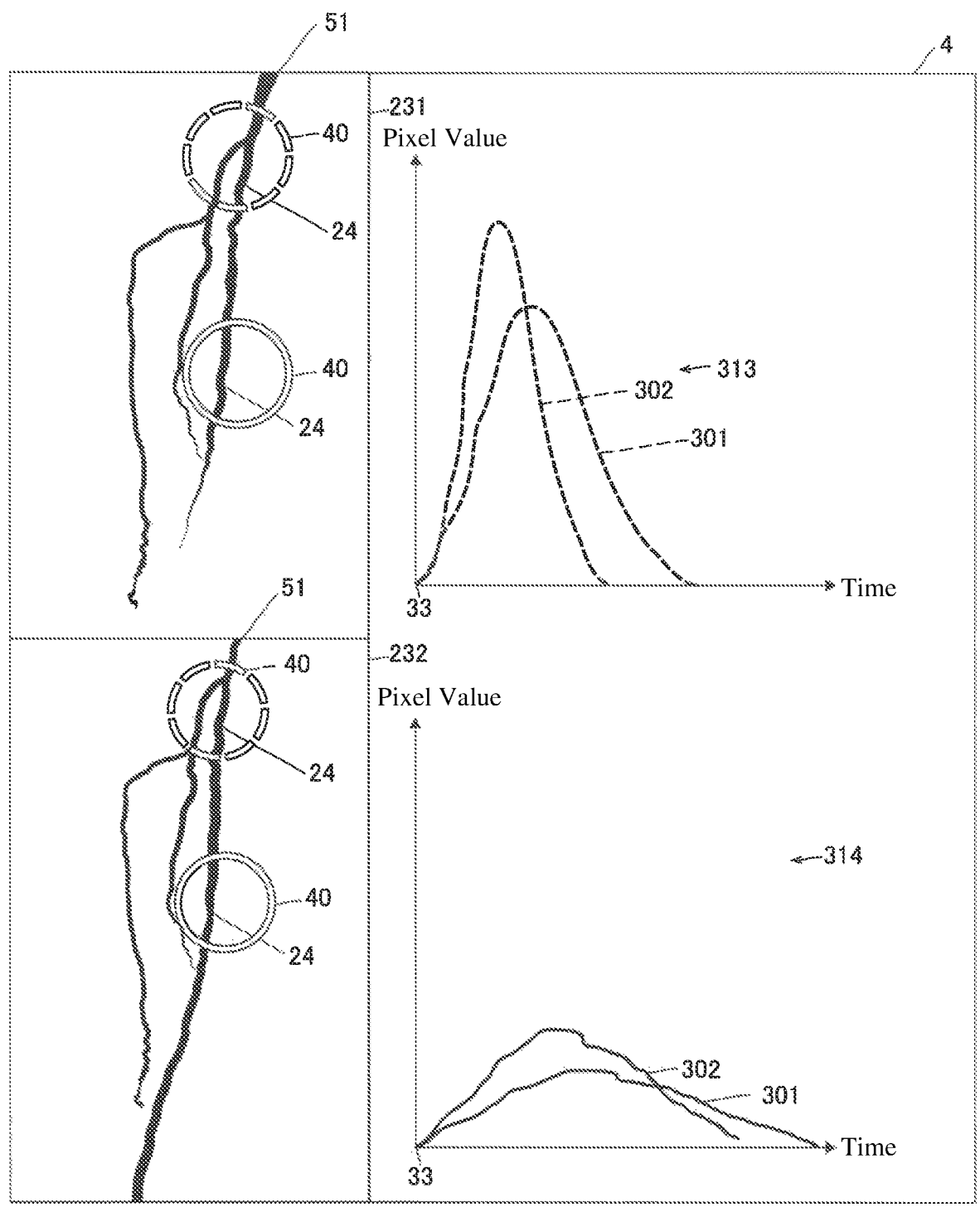
FIG. 9 is a diagram showing an example of a third concentration change image.
Figure 10:
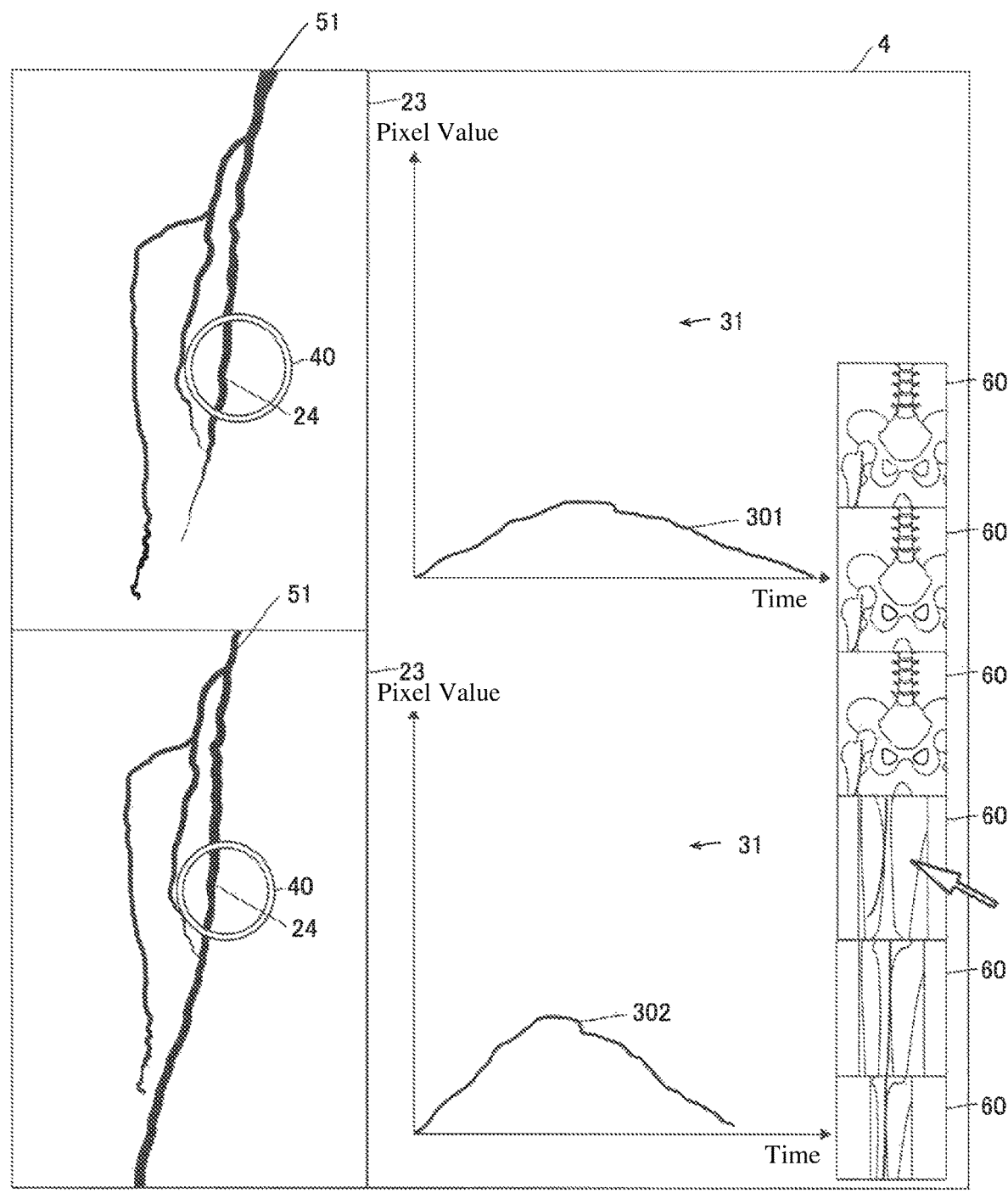
FIG. 10 is a diagram showing an example of thumbnail images.

Referring to FIG. 8, the case in which a first blood vessel image 231 and a second blood vessel image 232 are displayed on the display unit 4 will be described. In FIG. 8 to FIG. 10, the first blood vessel image 231 and the second blood vessel image 232 are used to explain that there are two blood vessel images 23. Also, a first concentration change image 311, a second concentration change image 312, and third concentration change images 313 and 314 are used to explain that there are four concentration change images 31. In the display unit 4, the first blood vessel image 231 and the second blood vessel image 232 are displayed side by side in the vertical direction. Further, in the display unit 4, the first blood vessel image 231 and the first concentration change image 311 are displayed side by side, and the second blood vessel image 232 and the second concentration change image 312 are displayed side by side.

When the target region 24 of the first blood vessel image 231 is selected, the control unit 3 performs control for selecting the target region 24 of the second blood vessel image 232 corresponding to the target region 24 of the first blood vessel image 231. Then, the control unit 3 performs control for displaying the region specification image 40 representing the target region 24 of the second blood vessel image 232 on the display unit 4 so as to be superimposed on the second blood vessel image 232.

As shown in FIG. 9, the image acquisition unit 2 generates a third concentration change image 313 in which the first concentration change image 311 in the target region 24 of the first blood vessel image 231 and the second concentration change image 312 in the target region 24 of the second blood vessel image 232 are superimposed with the reference points 33 aligned. Specifically, the image acquisition unit 2 generates the third concentration change image 313 by superimposing the graph image 301 included in the first concentration change image 311 and the graph image 302 included in the second concentration change image 312 with the reference points 33 aligned. When a plurality of target regions 24 is selected, the image acquisition unit 2 generates a third concentration change image 313 by superimposing the graph image 301 and the graph image 302 for each target region 24. The reference point 33 is a rising position of the graph image 30 at which the pixel value starts to increase.

The control unit 3 performs control for displaying on the display unit 4 the third concentration change image 313 in which the graph image 301 and the graph image 302 are superimposed.

When the operation unit 5 is operated by a user to switch the mode, the control unit 3 switches between the control for displaying the concentration change image 31 corresponding to a plurality of target regions 24 of the same blood vessel image 23 and the control for displaying the third concentration change image 313.

(Display of Thumbnail Image)

As shown in FIG. 10, the image acquisition unit 2 generates thumbnail images 60 as a list of a plurality of blood vessel images 23. When a blood vessel 51 of a lower limb is an imaging target, the imaging unit 1 cannot image the entire lower limb at a time, and therefore captures blood vessel images 23 by dividing the lower limb into a plurality of sections. For this reason, the thumbnail images 60 include blood vessel images 23 reflecting various lower limb sections.

The control unit 3 performs control for displaying the thumbnail images 60 on the display unit 4. When the display unit 4 shows a blood vessel image 23 and a concentration change image 31, the thumbnail images 60 are displayed at a position that does not overlap the blood vessel image 23 and the concentration change image 31. That is, the blood vessel image 23 (the first blood vessel image 231, the second blood vessel image 232), the concentration change image 31 (the first concentration change image 311, the second concentration change image 312, the third concentration change image 313 and 314), and the thumbnail image 60 are displayed at positions that are not overlapped with each other.

Figure 11:
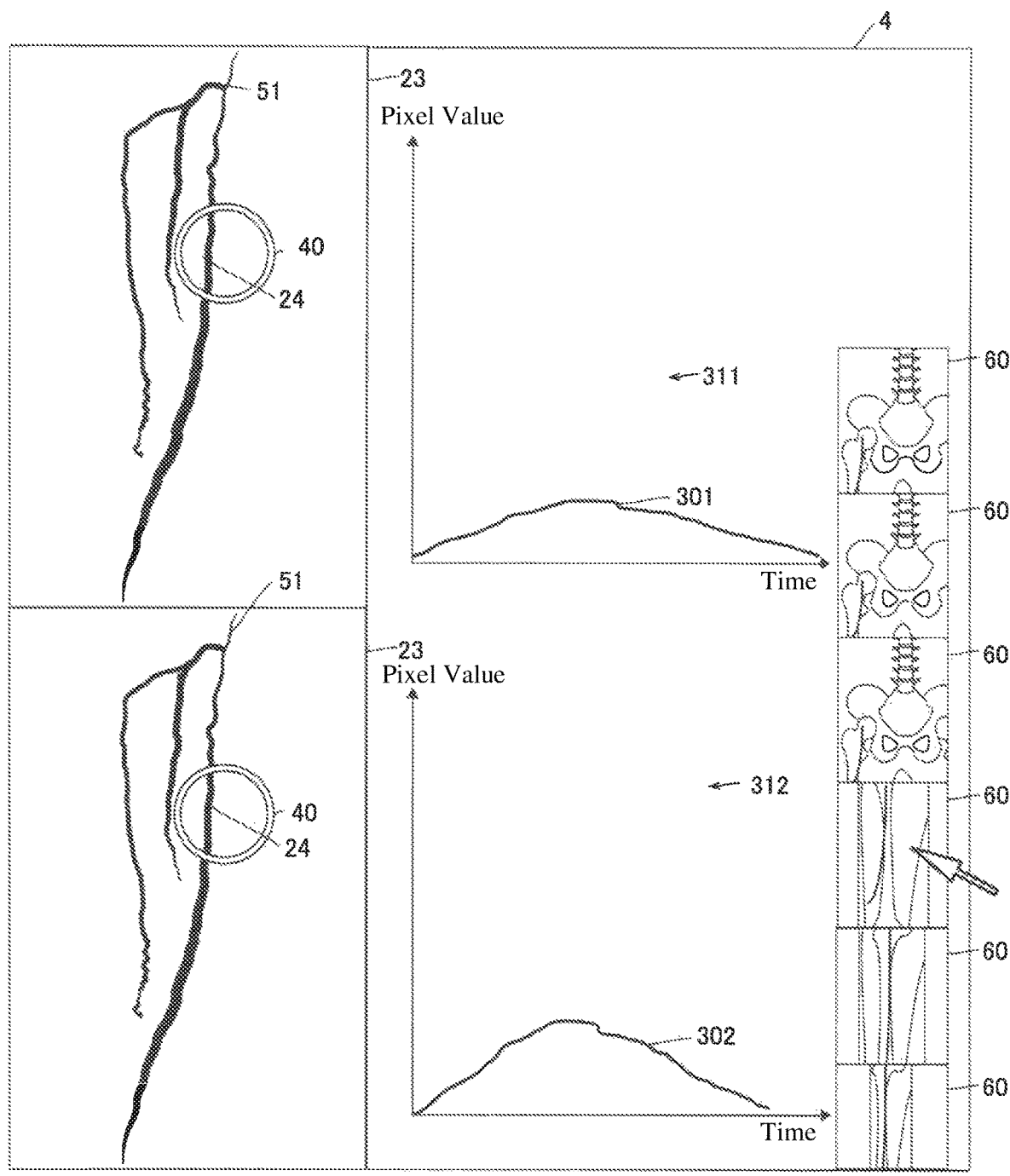
FIG. 11 is a diagram for explaining the switching of a blood vessel image.

As shown in FIG. 10 and FIG. 11, when one blood vessel image 23 is selected from the thumbnail images 60 by the operation unit 5, the control unit 3 switches the blood vessel image 23 displayed on the display unit 4 to the selected blood vessel image 23. Then, when a target region 24 is selected by the user input, the control unit 3 performs control for displaying a concentration change image 31 including the corresponding graph image 30 on the display unit 4. In FIG. 10, the arrow is shown to explain that the blood vessel image 23 is selected from the thumbnail images 60.

(Control Processing of Image Processing Apparatus)

Figure 12:
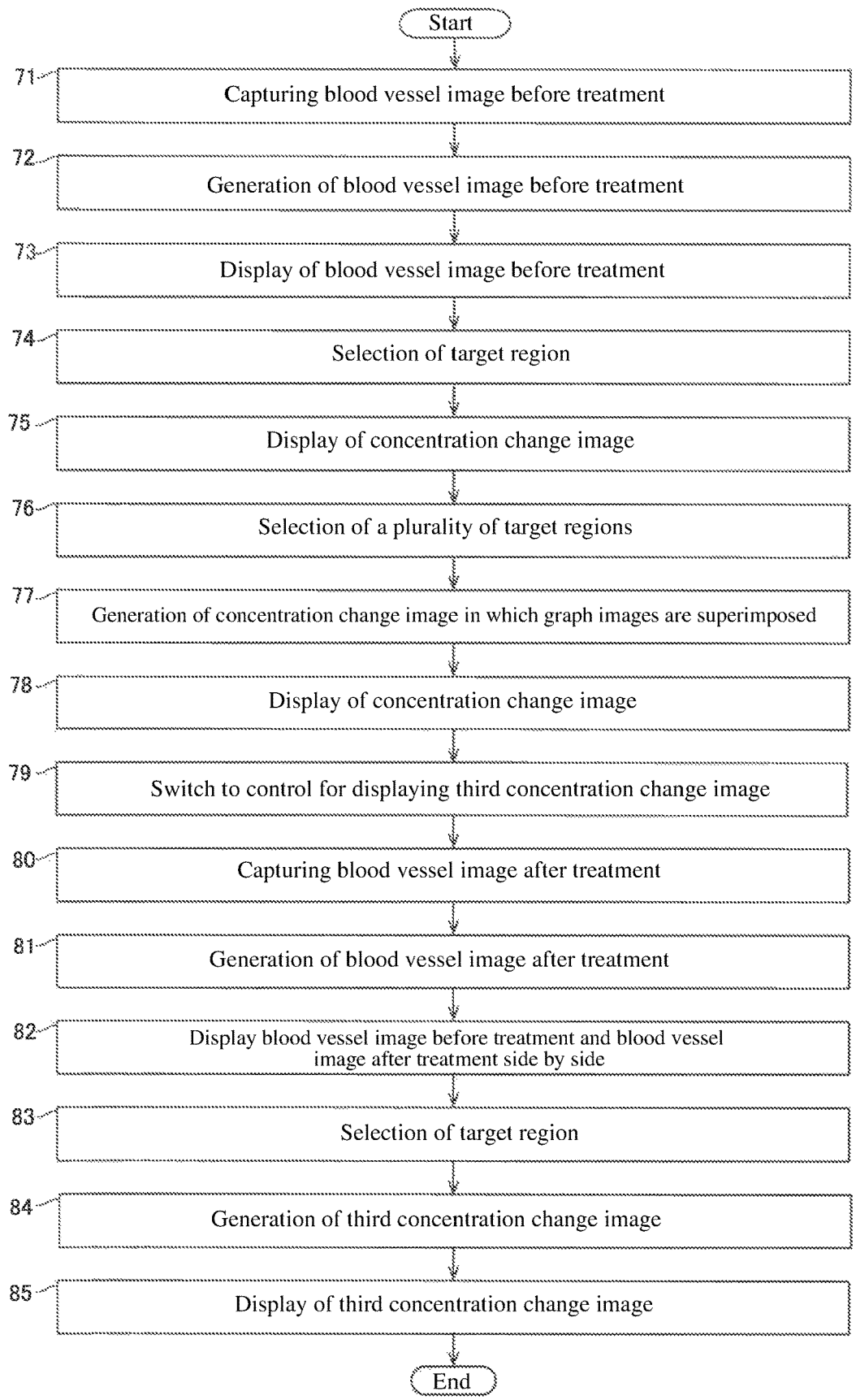
FIG. 12 is a flowchart for explaining the control processing of an image processing apparatus.

Referring to FIG. 12, the control processing of the image processing apparatus 100 will be described. In this embodiment, the image processing apparatus 100 is used to observe the restoration of the blood flow after the treatment of the subject 50 as a patient.

In Step 71, the imaging unit 1 captures a blood vessel image 23 before the treatment of the subject 50. In Step 72, the image acquisition unit 2 generates a concentration change image 31 including the blood vessel image 23 before the treatment and a graph image 30 after the treatment. Note that the blood vessel image 23 before the treatment is an example of the "first blood vessel image" described in claims and that the concentration change image 31 including the graph image 30 before the treatment is an example of the "first concentration change image" described in claims.

In Step 73, the control unit 3 performs control for displaying the generated blood vessel image 23 before the treatment on the display unit 4. In Step 74, the control unit 3 performs control for selecting the target region 24 from the blood vessel image 23 displayed on the display unit 4.

In Step 75, the control unit 3 performs control for displaying the concentration change image 31 including the graph image 30 of the selected target region 24. In Step 76, in accordance with the user's input, the control unit 3 performs control for selecting a plurality of target regions 24. In Step 77, the image acquisition unit 2 generates a concentration change image 31 in which graph images 30 respectively corresponding to the plurality of selected target regions 24.

In Step 78, the control unit 3 performs control for displaying the generated concentration change image 31 on the display unit 4.

In Step 79, in accordance with the user's input, the control unit 3 performs control for switching the control of displaying the concentration change image 31 on the display unit 4 to the control of displaying the third concentration change image 313.

In Step 80, the imaging unit 1 captures a blood vessel image 23 after the treatment of the subject 50. In Step 81, the image acquisition unit 2 generates a blood vessel image 23 after the treatment and a concentration change image 31 including graph images 30 after the treatment. Note that the blood vessel image 23 after the treatment is an example of the "second blood vessel image" recited in claims and that the concentration change image 31 including graph images 30 after the treatment is an example of the "second concentration change image" recited in claims.

In Step 82, the control unit 3 performs control for displaying the blood vessel image 23 before the treatment and the blood vessel image 23 after the treatment side by side on the display unit 4. In Step 83, in accordance with the user's input, the control unit 3 performs control for selecting a target region 24.

In Step 84, the image acquisition unit 2 generates a third concentration change image 131 in which the concentration change image 31 including the graph image 30 of the blood vessel image 23 before the treatment and the concentration change image 31 including the graph image 30 of the blood vessel image 23 after the treatment are superimposed with the reference points 33 aligned. In Step 85, the control unit 3 performs control for displaying the third concentration change image 313 on the display unit 4.

(Effects of this Embodiment)

In this embodiment, the following effects can be obtained.

In this embodiment, the image processing apparatus 100 is provided with an imaging unit 1 including an X-ray irradiation unit 11 for irradiating a subject 50 with X-rays and a detection unit 12 for detecting the X-rays passed through the subject 50 to acquire a detection signal, an image acquisition unit 2 for acquiring a blood vessel image 23 of the subject 50 based on a detection signal and generating a concentration change image 31 including graph images 30 indicating a temporal change of a value related to a concentration of a contrast agent administered to a blood vessel 51 of the subject 50, and a control unit 3 for performing control for displaying the blood vessel image 23 and the concentration change image 31 on the display unit 4. The control unit 3 is configured to perform control for accepting a selection of a target region 24 on the blood vessel image 23 displayed on the display unit 4 and for displaying the concentration change image 31 corresponding to the selected target region 24.

With this configuration, the concentration change image 31 corresponding to the target region 24 selected on the blood vessel image 23 is displayed, so that the user can intuitively grasp the blood flow velocity in the target region 24 of the blood vessel 51 from the concentration change image 31.

Further, in this embodiment, a plurality of target regions 24 of the blood vessel image 23 is configured to be selected. The image acquisition unit 2 is configured to generate the concentration change image 31 in which the graph images 30 respectively corresponding to the plurality of selected target regions 24 are superimposed. The control unit 3 is configured to perform control for displaying on the display unit 4 the concentration change image 31 in which the graph images 30 respectively corresponding to the plurality of target regions 24 are superimposed.

With this configuration, since the graph images 30 respectively corresponding to the plurality of target regions 24 are displayed in a superimposed manner on the display unit 4, the user can compare the concentration change images 31 corresponding to the plurality of target regions 24 while visually viewing the concentration change image 31 at the same time. With this, the visibility of the user can be improved.

Further, in this embodiment, the image acquisition unit 2 is configured to generate a graph image 30 of a waveform of a concentration change and is configured to generate a concentration change image 31 in which the graph images 30 are superimposed with the reference points 33 aligned to compare the widths 32 of the waveforms of the concentration changes.

By configuring as described above, since it becomes easy to compare the widths 32 of the waveforms of the concentration changes each indicating the time from the concentration of the contrast image starts to increase until the concentration of the contrast agent decreases and finally becomes a constant via the position of the peak which is the maximum concentration of the contrast agent with the reference points 33 aligned, it is possible to easily compare the contrast agent's flow velocities that the contrast agent flows the plurality of target regions 24.

Also, in this embodiment, the image acquisition unit 2 is configured to generate a concentration change image 31 in which the graph images 30 are superimposed with either one of the position of the peak at which the value related to the concentration of the contrast agent becomes maximum and the rising position at which the value related to the concentration of the contrast agent starts to increase as a reference point 33.

By configuring as described above, since the rising position and the peak position become a reference for comparing the magnitudes of the widths 32 of the waveforms of the concentration changes, it is possible to more easily compare the contrast agent's flow velocities in the plurality of target regions 24 based on the rising position and the peak position.

Further, in this embodiment, the image acquisition unit 2 generates the blood vessel image 23 discriminated according to the flow velocity of the contrast agent in the target region 24. By configuring as described above, the user can confirm the magnitude of the flow velocity of the contrast agent from the blood vessel image 23 in addition to the concentration change image 31.

Further, in this embodiment, the image acquisition unit 2 is configured to generate the first blood vessel image 231 and the second blood vessel image 232. When the target region 24 of the first blood vessel image 231 is selected, the target region 24 of the second blood vessel image 232 corresponding to the target region 24 of the selected first blood vessel image 231 is configured to be selected. The control unit 3 is configured to perform control for displaying the first concentration change image 311 corresponding to the target region 24 of the first blood vessel image 231 and the second concentration change image 312 corresponding to the target region 24 of the second blood vessel image 232 side by side on the display unit 4.

By configuring as described above, since the first concentration change image 311 and the second concentration change image 312 are displayed simultaneously, the user can easily compare the first concentration change image 311 and the second concentration change image 312. As a result, it is possible to easily compare the velocities that the contrast agent flows in the corresponding target regions 24 in the first concentration change image 311 and the second concentration change image 312.

Further, in this embodiment, the control unit 3 is configured to perform control for displaying on display unit 4 the third concentration change image 313 in which the first concentration change image 311 and the second concentration change image 312 are superimposed. By configuring as described above, the first concentration change image 311 and the second concentration change image 312 can be compared more easily by the third concentration change image 313. As a result, it is possible to more easily compare the flow velocities of the contrast agent in the corresponding target regions 24 in the first concentration change image 311 and the second concentration change image 312.

Further, in this embodiment, the control unit 3 is configured to switch between the control for displaying on the display unit 4 the concentration change images 31 in which the graph images corresponding to the plurality of target regions 24 of the first blood vessel image 231 or the second blood vessel image 232 are superimposed and the control for displaying on the display unit 4 the third concentration change image 313. By configuring as described above, the user can switch the displays according to the blood vessel image 23 which is desired to compare the contrast agent's flow velocities.

Further, in this embodiment, the image acquisition unit 2 is configured to superimpose the region specification image 40 indicating the target region 24 of the blood vessel image 23 on the blood vessel image 23. The control unit 3 is configured to perform control for displaying on the display unit 4 the image in which the region specification image 40 and the blood vessel image 23 are superimposed and the concentration change image 31. By configuring as described above, it is possible to confirm at a glance that the concentration change image 31 displayed on the display unit 4 corresponds to which part of the blood vessel image 23.

Further, in this embodiment, the control unit 3 is configured to perform control for calculating the representative value of the pixel value included in the region specification image 40 superimposed on the blood vessel image 23. The image acquisition unit 2 is configured to generate the concentration change image 31 based on the calculated representative value. By configuring as described above, by obtaining the representative value, noises due to variations in pixel value included in the region specification image 40 can be reduced.

Furthermore, this embodiment is further provided with the operation unit 5 for accepting an input operation by a user, and is configured to select the target region 24 of the blood vessel image 23 based on the input operation. By configuring as described above, the user can select the target region 24 at which the concentration change image 31 is desired to be confirmed.

Also, in this embodiment, the image acquisition unit 2 is configured to generate thumbnail images 60, which are images as a list of blood vessel images 23. The control unit 3 is configured to perform control for switching the blood vessel image 23 and the concentration change image 31 of the blood vessel image 23 displayed on the display unit 4 to the selected blood vessel image 23 and the selected concentration change image 31, when the blood vessel image 23 is selected from the thumbnail images 60. By configuring as described above, when it is desired to select a portion of the blood vessel 51 which is not included in the blood vessel image 23 displayed on the display unit 4 as a target region 24, it is possible to easily switch to the blood vessel image 23 including the portion of the blood vessel 51.

Also, in this embodiment, the image acquisition unit 2 is configured to generate a contrast agent image 21 based on a detection signal acquired using a contrast agent, generate a non-contrast agent image 22 based on a detection signal acquired without using a contrast agent, and generate a subtraction image 230 as a blood vessel image 23 by subtracting the non-contrast agent image 22 from the contrast agent image 21. The control unit 3 is configured to perform control for displaying on the display unit 4 the subtraction image 230 and the concentration change image 31 corresponding to the target region 24 of the selected blood vessel image 23. By configuring as described above, since the subtraction image 230 is an image in which the blood vessel 51 is clearly reflected, the user can grasp the position of the blood vessel 51.

(Modifications)

It should be noted that the embodiments disclosed herein are to be considered in all respects as illustrative and not restrictive. The scope of the present invention is indicated by claims rather than by the above-described description of the embodiment, and includes all changes (modifications) within the meanings and scopes equivalent to claims.

For example, in the above-described embodiment, an example is shown in which the imaging position of the blood vessel image is a blood vessel of a lower limb, but the present invention is not limited thereto. For example, the imaging position of the blood vessel image may be a blood vessel of an arm.

In the above-described embodiment, an example is shown in which the value related to the concentration of the contrast agent is a pixel value of the target region, but the present invention is not limited thereto. For example, the numerical value related to the concentration of the contrast agent may be a concentration of a contrast agent in the target region.

In the above-described embodiment, an example is shown in which the concentration change image includes a graph image indicating the temporal change of the value related to the concentration of the contrast agent, but the present invention is not limited thereto. For example, the concentration change image may include a numerical value related to the concentration of the contrast agent.

In the above-described embodiment, an example is shown in which the display unit is a monitor provided in the image processing apparatus, but the present invention is not limited thereto. For example, the display unit may be an external monitor connected to the image processing apparatus.

In the above-described embodiment, an example is shown in which the target region is selected by a user, but the present invention is not limited thereto. For example, the image acquisition unit may depict a characteristic portion from the blood vessel image, and the control unit may automatically select the target region based on the characteristic portion.

Further, in the above-described embodiment, an example is shown in which the target region of the blood vessel image is selected at two points, but the present invention is not limited thereto. For example, the target region of the blood vessel image may be selected at three or more points.

Further, in the above-described embodiment, an example is shown in which the graph image is a waveform of a concentration change, but the present invention is not limited thereto. For example, a bar graph may be used if the concentration change can be acquired.

Further, in the above-described embodiment, an example is shown in which the reference point is a rising position, but the present invention is not limited thereto. For example, the reference point may be a peak position at which the numerical value indicating the concentration of the contrast agent is highest.

Further, in the above-described embodiment, an example is shown in which in the blood vessel image identification method in which the velocity is displayed so as to be visually distinguishable in accordance with the flow velocity of the contrast agent, the portion where the flow velocity of the contrast agent is fast is displayed in red and the portion where the flow velocity is slow is displayed in blue, but the present invention is not limited thereto. As long as it is discriminable, it may be represented using, for example, black and white, or may be numbered or labeled.

Further, in the above-described embodiment, an example is shown in which when the target region of the first blood vessel image is selected, the target region of the second blood vessel image corresponding to the target region of the selected first blood vessel image is selected, but the present invention is not limited thereto. For example, when the target region of the second blood vessel image is selected, the target region of the first blood vessel image corresponding to the target region of the selected second blood vessel image may be selected.

Further, in the above-described embodiment, an example is shown in which two blood vessel images, i.e., the first blood vessel image and the second blood vessel image, are displayed on the display unit, but the present invention is not limited thereto. For example, three or more blood vessel images may be displayed on the display unit.

Further, in the above-described embodiment, an example is shown in which the control unit is capable of switching between the control for displaying on the display unit the concentration change image in which graph images are superimposed on the respective plurality of target regions of the first blood vessel image or the second blood vessel image and the control for displaying the display unit the third concentration change image, but the present invention is not limited thereto. For example, the control unit may be controlled so as to perform the control for displaying on the display unit the concentration change image in which the graph image corresponding to each of the plurality of target regions of the first blood vessel image or the second blood vessel image is superimposed and the control for displaying on the display unit the third concentration change image.

Further, in the above-described embodiment, an example is shown in which the region specification image is displayed by a solid circular line and a broken circular line, but the present invention is not limited thereto. For example, the color to be displayed may be changed or the shape may be changed if it is discriminable. The shape of the region specification image may be a figure such as a square other than a circle.

Further, in the above-described embodiment, an example is shown in which the image acquisition unit averages the pixel values included in the range of the region specification image and generates the concentration change image based on the average value, but the present invention is not limited thereto. For example, the image acquisition unit may calculate the average value of the pixel values included in the range of the region specification image or may calculate the sum value.

Further, in the above embodiment, an example is shown in which the operation unit is a touch panel, but the present invention is not limited thereto. For example, the operation unit may be a console such as a mouse.

Further, in the above-described embodiment, an example is shown in which the user selects the target region when the blood vessel image displayed on the display unit is switched, but the present invention is not limited thereto. For example, a blood vessel image after switching the setting of the position of the target region that was set to the blood vessel image before the switching may be used for the blood vessel image after the switching.

Further, in the above-described embodiment, an example is shown in which the subtraction image is used as a blood vessel image, but the present invention is not limited thereto. For example, a contrast agent image may be used as a blood vessel image.

(Modification of Control Processing of Image Processing Apparatus)

Figure 13:
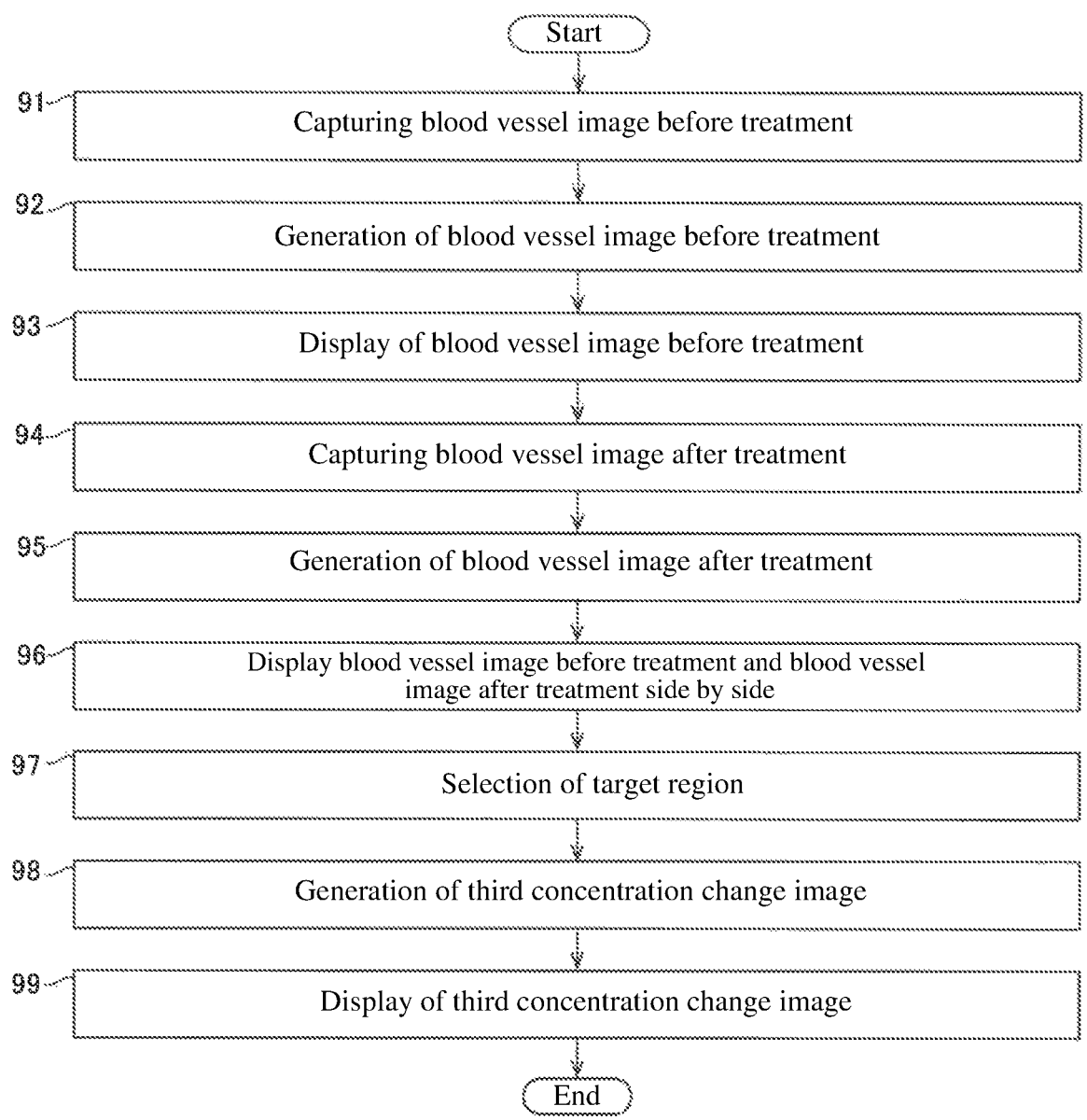
FIG. 13 is a flowchart for explaining a modification of control processing of an image processing apparatus.

In the above-described embodiment, the control processing of the image processing apparatus shown in FIG. 12 is exemplified, but the present invention is not limited thereto. As in the example shown in FIG. 13, it is not necessary to execute any of the control processing shown in FIG. 12. Referring to FIG. 13, a modification of the image processing of the image processing apparatus will be described. In the modification, the selection of the target region is performed after obtaining the blood vessel image before the treatment and the blood vessel image after the treatment.

In Step 91, the imaging unit performs imaging of a blood vessel image before the treatment of the subject. In Step 92, the image acquisition unit generates a concentration change image including a blood vessel image before the treatment and a graph image before the treatment.

In Step 93, the control unit performs control for displaying the generated blood vessel image before the treatment on the display unit.

In Step 94, the imaging unit performs imaging of the blood vessel image after the treatment of the subject. In Step 95, the image acquisition unit generates a concentration change image including the blood vessel image after the treatment and a graph image after the treatment.

In Step 96, the control unit performs control for displaying the blood vessel image before the treatment and the blood vessel image after the treatment on the display unit side by side. In Step 97, in accordance with the input by a user, the control unit performs control for selecting the target region.

In Step 98, the image acquisition unit generates a third concentration change image in which the concentration change image including the graph image of the blood vessel image before the treatment and the concentration change image including the graph image of the blood vessel image after the treatment are superimposed with the reference points aligned. In Step 99, the control unit performs control for displaying the third concentration change image on the display unit.

ASPECTS

It will be understood by those skilled in the art that the above-described exemplary embodiments are concrete examples of the following aspects.

(Item 1)

An image processing apparatus comprising:

an imaging unit including an X-ray irradiation unit configured to emit X-rays to a subject and a detection unit configured to detect the X-rays transmitted through the subject to acquire a detection signal;

an image acquisition unit configured to acquire a blood vessel image of the subject based on the detection signal and generate a concentration change image including a graph image indicating a temporal change of a value related to a concentration of a contrast agent administered to a blood vessel of the subject; and a control unit configured to perform control for displaying the blood vessel image and the concentration change image on a display unit, wherein the control unit is configured to perform control for accepting a selection of a target region on the blood vessel image displayed on the display unit and perform control for displaying the concentration change image corresponding to the selected target region.

(Item 2)

The image processing apparatus as recited in the aforementioned Item 1, wherein it is configured to be able to select a plurality of target regions on the blood vessel image, wherein the image acquisition unit is configured to generate the concentration change image in which the graph images respectively corresponding to the selected plurality of target regions are superimposed, and wherein the control unit is configured to perform control for displaying the concentration change image in which the graph images respectively corresponding to the plurality of target regions are superimposed on the display unit.

(Item 3)

The image processing apparatus as recited in the aforementioned Item 2, wherein the image acquisition unit is configured to generate the graph images of waveforms of concentration changes and generate the concentration change image in which the graph images are superimposed with reference points thereof aligned to compare widths of the waveforms of the concentration changes.

(Item 4)

The image processing apparatus as recited in the aforementioned Item 3, wherein the image acquisition unit is configured to generate the concentration change image in which the graph images are superimposed with either one of a peak position at which a value related to a concentration of the contrast agent becomes highest and a rising position at which the value related to the concentration of the contrast agent starts to increase as the reference point.

(Item 5)

The image processing apparatus as recited in any one of the aforementioned Items 1 to 4, wherein the image acquisition unit generates the blood vessel image in which a flow velocity of the contrast agent in the target region is visually recognizably displayed depending on to the flow velocity.

(Item 6)

The image processing apparatus as recited in any one of the aforementioned Items 1 to 5, wherein the image acquisition unit is configured to generate a first blood vessel image and a second blood vessel image, wherein it is configured such when the target region of the first blood vessel image is selected, the target region of the second blood vessel image corresponding to the target region of the selected first blood vessel image is selected, and wherein the control unit is configured to perform control for displaying a first concentration change image corresponding to the target region of the first blood vessel image and a second concentration change image corresponding to the target region of the second blood vessel image side by side on the display unit.

(Item 7)

The image processing apparatus as recited in the aforementioned Item 6, wherein the control unit is configured to perform control for displaying a third concentration change image in which the first concentration change image and the second concentration change image are superimposed on the display unit.

(Item 8)

The image processing apparatus as recited in the aforementioned Item 7, wherein the control unit is configured to switch between control for displaying the concentration change image in which the graph images respectively corresponding to the plurality of target regions of the first blood vessel image or the second blood vessel image are superimposed on the display unit and control for displaying the third concentration change image on the display unit.

(Item 9)

The image processing apparatus as recited in any one of the aforementioned Items 1 to 8, wherein the image acquisition unit is configured to superimpose a region specification image showing the target region of the blood vessel image on the blood vessel image, and wherein the control unit is configured to perform control for displaying an image in which the region specification image and the blood vessel image are superimposed and the concentration change image on the display unit side by side.

(Item 10)

The image processing apparatus as recited in the aforementioned Item 9, wherein the control unit is configured to perform control for calculating a representative value of a pixel value included in the region specification image displayed on the blood vessel image in a superimposed manner, and wherein the image acquisition unit is configured to generate the concentration change image based on the calculated representative value.

(Item 11)

The image processing apparatus as recited in any one of the aforementioned Items 1 to 10, further comprising:

an operation unit configured to accept an input operation by a user, wherein the target region of the blood vessel image is selected based on the input operation.

(Item 12)

The image processing apparatus as recited in any one of the aforementioned Items 1 to 11, wherein the image acquisition unit is configured to generate thumbnail images which are images constituted as a list of blood vessel images, and wherein when the blood vessel image is selected from the thumbnail images, the control unit is configured to perform control for switching the blood vessel image and the concentration change image displayed on the display unit to the selected blood vessel image and the concentration change image of the selected blood vessel image.

(Item 13)

The image processing apparatus as recited in any one of the aforementioned Items 1 to 12, wherein the image acquisition unit is configured to generate a contrast agent image based on the detection signal acquired using the contrast agent, generate a non-contrast agent image based on the detection signal acquired without using the contrast agent, and generate a subtraction image as the blood vessel image by subtracting the non-contrast agent image from the contrast agent image, and wherein the control unit is configured to perform control for displaying the subtraction image and the concentration change image corresponding to the target region of the selected blood vessel image side by side on the display unit.

The invention claimed is:

1. An image processing apparatus comprising:
an imaging unit including an X-ray irradiation unit configured to emit X-rays to a subject and a detection unit configured to detect the X-rays transmitted through the subject to acquire a detection signal;
an image acquisition unit configured to acquire a blood vessel image of the subject based on the detection signal and generate a concentration change image including a graph image indicating a temporal change of a value related to a concentration of a contrast agent administered to a blood vessel of the subject; and
a control unit configured to perform control for displaying the blood vessel image and the concentration change image on a display unit,
wherein the control unit is configured to perform control for accepting a selection of a target region on the blood vessel image displayed on the display unit and perform control for displaying the concentration change image corresponding to the selected target region,
wherein the image acquisition unit is configured to generate a first blood vessel image and a second blood vessel image,
wherein it is configured such that when the target region of the first blood vessel image is selected, a target region of the second blood vessel image corresponding to the target region of the selected first blood vessel image is selected, and
wherein the control unit is configured to perform control for displaying a first concentration change image corresponding to the target region of the first blood vessel image and a second concentration change image corresponding to the target region of the second blood vessel image on the display unit.

2. The image processing apparatus as recited in claim 1, wherein it is configured to be able to select a plurality of target regions on the blood vessel image,
wherein the image acquisition unit is configured to generate the concentration change image in which the graph images respectively corresponding to the selected plurality of target regions are superimposed, and
wherein the control unit is configured to perform control for displaying the concentration change image in which the graph images respectively corresponding to the plurality of target regions are superimposed on the display unit.

3. The image processing apparatus as recited in claim 2, wherein the image acquisition unit is configured to generate the graph images as waveforms of concentration changes and generate the concentration change image in which the graph images are superimposed with reference points thereof aligned to compare widths of the waveforms of the concentration changes.

4. The image processing apparatus as recited in claim 3, wherein the image acquisition unit is configured to generate the concentration change image in which the graph images are superimposed with either one of a peak position at which a value related to a concentration of the contrast agent becomes highest and a rising position at which the value related to the concentration of the contrast agent starts to increase as the reference point.

5. The image processing apparatus as recited in claim 1, wherein the image acquisition unit generates the blood vessel image in which a flow velocity of the contrast agent in the target region is visually recognizably displayed depending on the flow velocity.

6. The image processing apparatus as recited in claim 1, wherein the control unit is configured to perform control for displaying the first concentration change image and the second concentration change image side by side on the display unit.

7. The image processing apparatus as recited in claim 6, wherein the control unit is configured to perform control for displaying a third concentration change image in which the first concentration change image and the second concentration change image are superimposed on the display unit.

8. The image processing apparatus as recited in claim 7, wherein the control unit is configured to switch between control for displaying the concentration change image in which the graph images respectively corresponding to the target regions of the first blood vessel image or the second blood vessel image are superimposed on the display unit and control for displaying the third concentration change image on the display unit.

9. The image processing apparatus as recited in claim 1, wherein the image acquisition unit is configured to superimpose a region specification image showing the target region of the blood vessel image on the blood vessel image, and
wherein the control unit is configured to perform control for displaying an image in which the region specification image and the blood vessel image are superimposed on the concentration change image on the display unit side by side.

10. The image processing apparatus as recited in claim 9, wherein the control unit is configured to perform control for calculating a representative value of a pixel value included in the region specification image displayed on the blood vessel image in a superimposed manner, and
wherein the image acquisition unit is configured to generate the concentration change image based on the calculated representative value.

11. The image processing apparatus as recited in claim 1, further comprising:
an operation unit configured to accept an input operation by a user,
wherein the target region of the blood vessel image is selected based on the input operation.

12. The image processing apparatus as recited in claim 1, wherein the image acquisition unit is configured to generate thumbnail images which are images constituted as a list of blood vessel images, and
wherein when the blood vessel image is selected from the thumbnail images, the control unit is configured to perform control for switching the blood vessel image and the concentration change image displayed on the display unit to the selected blood vessel image and the concentration change image of the selected blood vessel image.

13. The image processing apparatus as recited in claim 1, wherein the image acquisition unit is configured to generate a contrast agent image based on the detection signal acquired using the contrast agent, generate a non-contrast agent image based on the detection signal acquired without using the contrast agent, and generate a subtraction image as the blood vessel image by subtracting the non-contrast agent image from the contrast agent image, and wherein the control unit is configured to perform control for displaying the subtraction image and the concentration change image corresponding to the target region of the selected blood vessel image side by side on the display unit.

* * * * *